(12) United States Patent
Maskin

(10) Patent No.: US 12,383,240 B1
(45) Date of Patent: Aug. 12, 2025

(54) INTRADUCTAL MEIBOMIAN GLAND PROBING WITH MICROTUBE USE

(71) Applicant: Steven L. Maskin, Tampa, FL (US)

(72) Inventor: Steven L. Maskin, Tampa, FL (US)

( * ) Notice: Subject to any disclaimer, the term of this patent is extended or adjusted under 35 U.S.C. 154(b) by 587 days.

(21) Appl. No.: 16/847,046

(22) Filed: Apr. 13, 2020

Related U.S. Application Data

(60) Provisional application No. 62/833,359, filed on Apr. 12, 2019.

(51) Int. Cl.
*A61B 10/00* (2006.01)

(52) U.S. Cl.
CPC .. *A61B 10/0045* (2013.01); *A61B 2010/0067* (2013.01)

(58) Field of Classification Search
None
See application file for complete search history.

(56) References Cited

U.S. PATENT DOCUMENTS

| | | | | |
|---|---|---|---|---|
| 2006/0154364 A1* | 7/2006 | Coroneo | ............... | A61P 27/02 435/325 |
| 2010/0100029 A1* | 4/2010 | Maskin | ............... | A61M 1/85 604/93.01 |
| 2010/0292630 A1* | 11/2010 | Maskin | ............... | A61F 9/0017 604/20 |
| 2012/0265101 A1* | 10/2012 | Korb | ............... | A61B 3/10 600/587 |
| 2013/0110101 A1* | 5/2013 | Van Valen | ............... | A61F 9/00718 606/33 |
| 2019/0247227 A1* | 8/2019 | Peyman | ............... | A61K 45/06 |

\* cited by examiner

*Primary Examiner* — Aurelie H Tu
(74) *Attorney, Agent, or Firm* — ALLEN, DYER, DOPPELT + GILCHRIST, P.A.

(57) ABSTRACT

A microtube is used to obtain a meibum sample from an intraductal space within a meibomian gland while avoiding contamination of the sample due to contact with the lid margin. The microtube can also be used as a gland marker providing a reference marker for subsequent visualization of one or more adjacent glands, as well as a stent for a meibomian gland having lining being repopulated with cells or replaced.

1 Claim, 6 Drawing Sheets

INTRADUCTAL MEIBOMIAN GLAND PROBING WITH MICROTUBE USE

CROSS-REFERENCE TO RELATED APPLICATION

This application claims the benefit of U.S. Provisional Patent Application Ser. No. 62/833,359, filed on Apr. 12, 2019, the contents of which are herein incorporated by reference in their entirety.

FIELD OF THE INVENTION

The present invention relates to the treatment of meibomian glands, and more particularly, to meibomian gland probing.

BACKGROUND OF THE INVENTION

Intraductal meibomian gland probing (as disclosed in U.S. Pat. No. 10,159,599, filed as International Patent Application No. PCT/US2008/083318 on Nov. 13, 2008—the contents of which are herein incorporated by reference in their entirety) was invented by the present inventor in the course of trying to better understand underlying causes of meibomian gland dysfunction. While intraductal meibomian gland probing has proven remarkably effective, even in its most basic forms, further improvements are believed possible with respect to both diagnosis and treatment if more targeted probing can be employed.

Intraductal probing is often conducted using slit lamp visualization, although this previously involved only viewing a color image through the slit lamp oculars. Such visualization typically only showed the probe entering through the orifice. Infrared imaging could show the probe within the gland; however, such imaging was not available to the practitioner in real-time.

DESCRIPTION OF THE INVENTION

Figure 1:
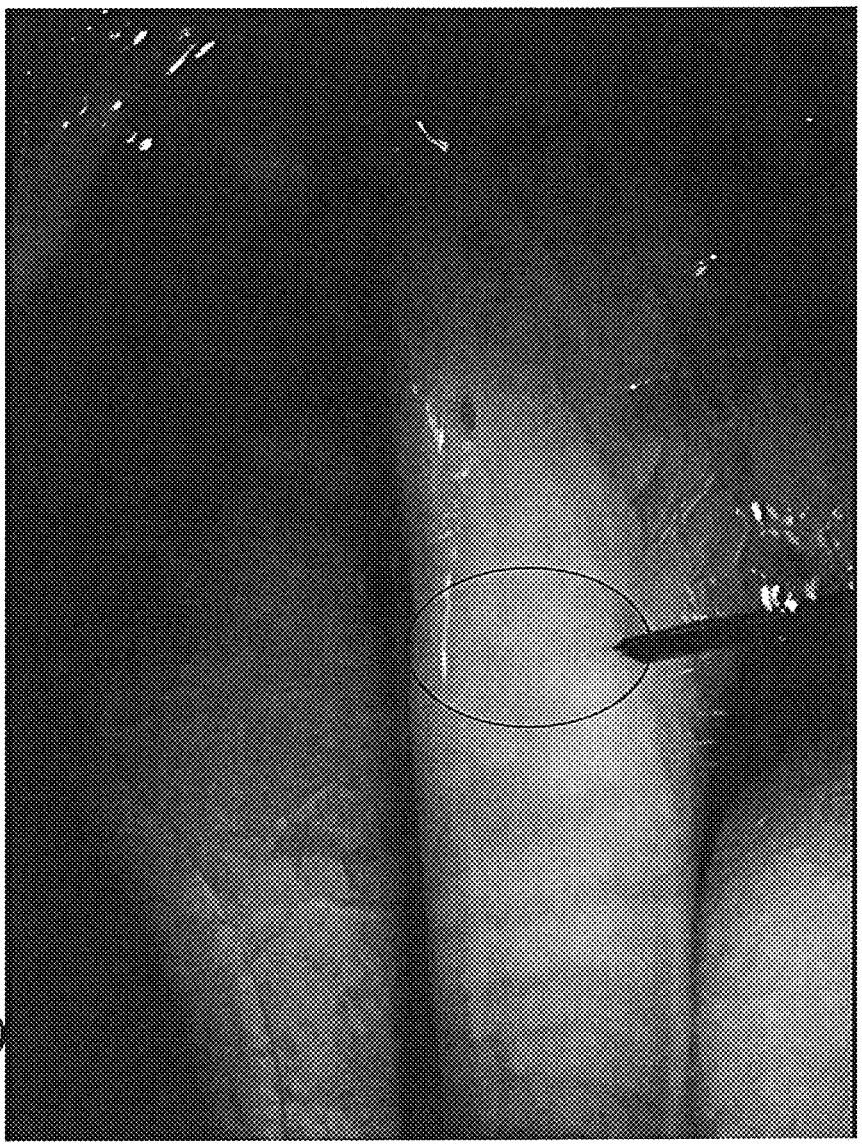
FIG. 1 shows a meibomian gland being probed which has a lack of normal appearing shape and optical density of acinar-ductule units in an organized presentation.

According to an embodiment of the present invention, meibomian gland probing (MGP) was performed on a real world patient. Preferably, one drop of topical 0.5% Tetracaine Hydrochloride was placed in the inferior fornix followed by placing a bandage contact lens over the cornea. Topical anesthetic ointment consisting of 8% lidocaine with 25% jojoba (JOA) in a petrolatum ointment base was applied to the inferior lid margin. The eye was closed for 15 minutes. A second application of JOA was applied when necessary. One additional drop of topical tetracaine was then placed in the eye. The patient was then positioned at the slit lamp and its infrared camera was activated. The lower lid was everted and the color image of the meibomian gland orifices and glands were focused through the slit lamp oculars while a separate monitor displayed the infrared image of the glands for inspection (utilizing a Mediworks™ S390L WDR FireFly™ Digital Slit Lamp from Eyefficient™ (Aurora, Ohio)). A 1 mm long stainless-steel sterile intraductal meibomian gland probe was then inserted into each orifice, perpendicular to the lid margin using a dart throwing motion to find the angle of entry.

This same feature of this slit lamp can be reproduced for an operating microscope in an operating or procedure room where the patient is lying supine. One advantage is not needing an assistant to hold the head in place. Also, at the slit lamp, the upper lids are not easily viewable with this technique as the everted lid orifices would face upwards making the probing difficult. However, with the patient lying supine, the orifices of the everted lid would be facing the doctor, facilitating this procedure. Another benefit of performing this procedure with supine patient is that the head is at a fixed focal distance while foot pedal focusing allows freeing up of one hand to help stabilize the lid during the procedure.

The probe could be seen through the oculars' color slit lamp image entering through the orifices only, while the monitor showed the infrared image of the entire probe entering and moving to and fro within the gland duct. As the probe was moved, the video image followed the probe real-time into the distal, mid and proximal duct up to the full length of 1, 2 and 4 mm probes. At times, the movement of the probe was completely directed by viewing the video monitor IR image and not looking through the slit lamp oculars. In this manner, the probe and microtube devices could be directed at selective parts of the proximal, mid or distal glands to deliver localized therapeutics or retrieve specimens.

As the probe passed through the orifice lumen and into the distal duct there typically was resistance to the probe. The resistance was characterized as fixed, firm, focal and unyielding (FFFUR). It required additional probing force to relieve, analogous to relief of punctal fibrosis with a canicular probe. Opening the obstruction created a tactile sensation of pressure release as well as audible "firm pop" (FP) and "firm gritty (multiple pops)" (FG) sound heard by patient and physician as the tight band of contracting periductal fibroses was released and resistance gave way, allowing sudden advancement of the probe which was then able to freely pass to and fro within the duct. Accompanying an audible FP was a single focus of pressure release while accompanying a FG were multiple foci. There was a variation in the intensity level of tactile intraductal resistance which was consistent with the audible volume generated by relief of the obstruction, at times heard across the room by family members, and thought to correlate with severity of obstruction. The FP and FG were sudden bursts of quick, not prolonged sounds. For FG, the multiple individual firm pop sounds could occur immediately after each other in rapid succession, or after a short delay where the probe advanced through an interim non-strictured course of duct lumen.

Less commonly, a mild back pressure or "soft" resistance (SFT) was noted which was not fixed, not firm and easily yielding. Soft resistance was felt, but allowed the probe to pass without significant additional mechanical pressure. Passing through SFT did not generate an audible sound. It can be thought of as providing "drag" on the "to and fro" movement of the wire probe. SFT was not focal in contrast to the FFFUR which characteristically was focal or multifocal. Infrequently, there was a lack of resistance designated as "NR" where the probe entered and penetrated the orifice and duct without any resistance or drag.

After removing the probe, a 1-2 mm long stainless steel microtube of 110 OD was introduced into the glands to inject therapeutic dexamethasone. The tube was visualized within glands under IR meibography conditions to inject of dexamethasone. To retrieve a sample of meibum from within the intraductal space, an alternative 4 mm long microtube was placed through the already probed dilated orifice and into the gland, visualized under IR meibography conditions. This microtube may be made from polyimide with an approximate OD of 125 and ID of 90 microns.

The 4 mm polyimide tube could be retained within a gland after pre-dilating with gland probing. This was confirmed with confocal microscopy showing presence of tube end inside orifice. As noted above, this tube was able to collect specimen from selective intraductal locations for analysis. Alternatively, the tube may remain in the gland to function as an in situ gland marker. Having a gland marker is a breakthrough in the ability to study an identical gland for short and long term effects from therapies and disease. This is accomplished by noting the status of a gland/orifice a certain number of orifice distances from the in situ gland marker. Glands are then evaluated with confocal microscopy and meibography. The stent also functions as an adjunct to maintain a patent duct channel in existing glands or when reconstructing a new gland in a previously atrophic location.

In lid margin locations characterized by whole gland atrophy (or focal atrophy), there may or not be a retained orifice. Without an orifice, probes can create a new orifice within the lid margin under real-time IR meibography monitoring and extend a central duct channel in continuity from the orifice any desired distance appropriate for that lid width up to approximately 6 mm perpendicular to lid margin. With a newly created or recreated central duct channel, a stent may be placed to retain this channel until the lining of the channel is repopulated with cells or replaced with a transplanted gland. Repopulation with patient's cells may be stimulated by using intraductal blood product injection such as autologous serum, PRP, umbilical cord blood and others as well as use of stem cell products, hormones, vitamins, growth factors and other factors. In this way, stimulated cell proliferation and differentiation reconstructs or replaces the atrophic gland. Alternatively, the gland may be replaced with gland transplantation using 3D printing technology.

Lower lid Meibomian Glands were visualized during the probing, microtube injection and meibum sample retrieval procedures. Glands were evaluated for whole gland atrophy, proximal or distal atrophy or disorganized appearance then correlated to probe findings of FFFUR or SFT or NR. Whole gland atrophy was identified where a gland showed no discernible gland elements for the full extent of the width. Proximal atrophy was defined as a lack of discernible gland elements at the proximal end of the gland. Distal atrophy was missing discernible acinar-ductule units from the distal end of the duct adjacent the orifice. The disorganized gland appearance was designated if the gland structure and morphology showed a lack of normal appearing shape and optical density of acinar-ductule units in an organized presentation (FIG. 1).

Figure 2:
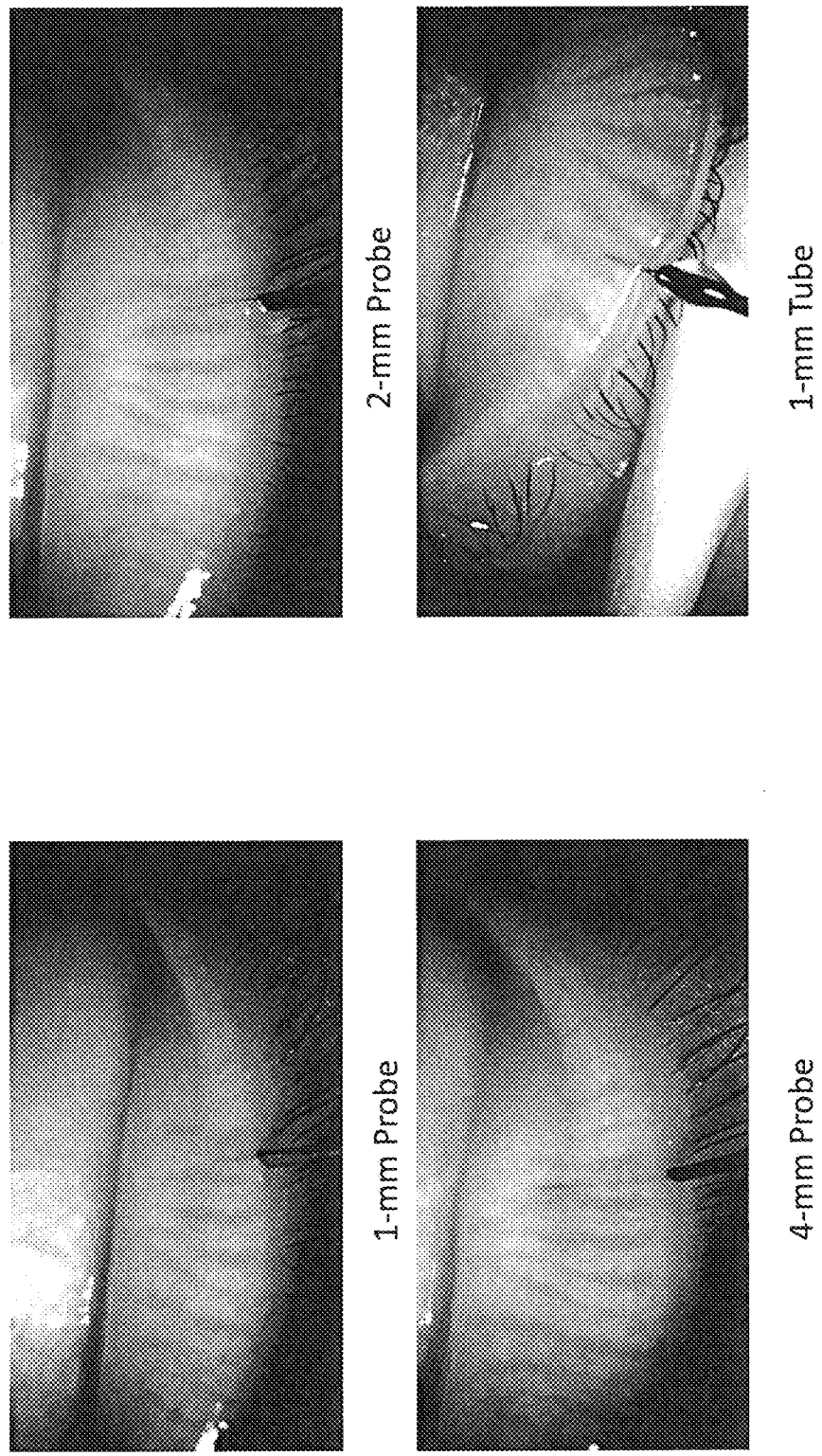
FIG. 2 is a composite of various meibomian glands being probed with different length probes.

Of 385 glands were probed from 14 lids, over 90% of the probes (1, 2 and 4 mm) could be visualized within the gland localized to the central duct. (FIG. 2 composite) The movement of the probes could be followed in real-time by viewing the IR image on the monitor. Monitoring the device location by viewing the monitor ensured safe location and enabled selective localization of device tip. There were no false passages.

Figure 3:
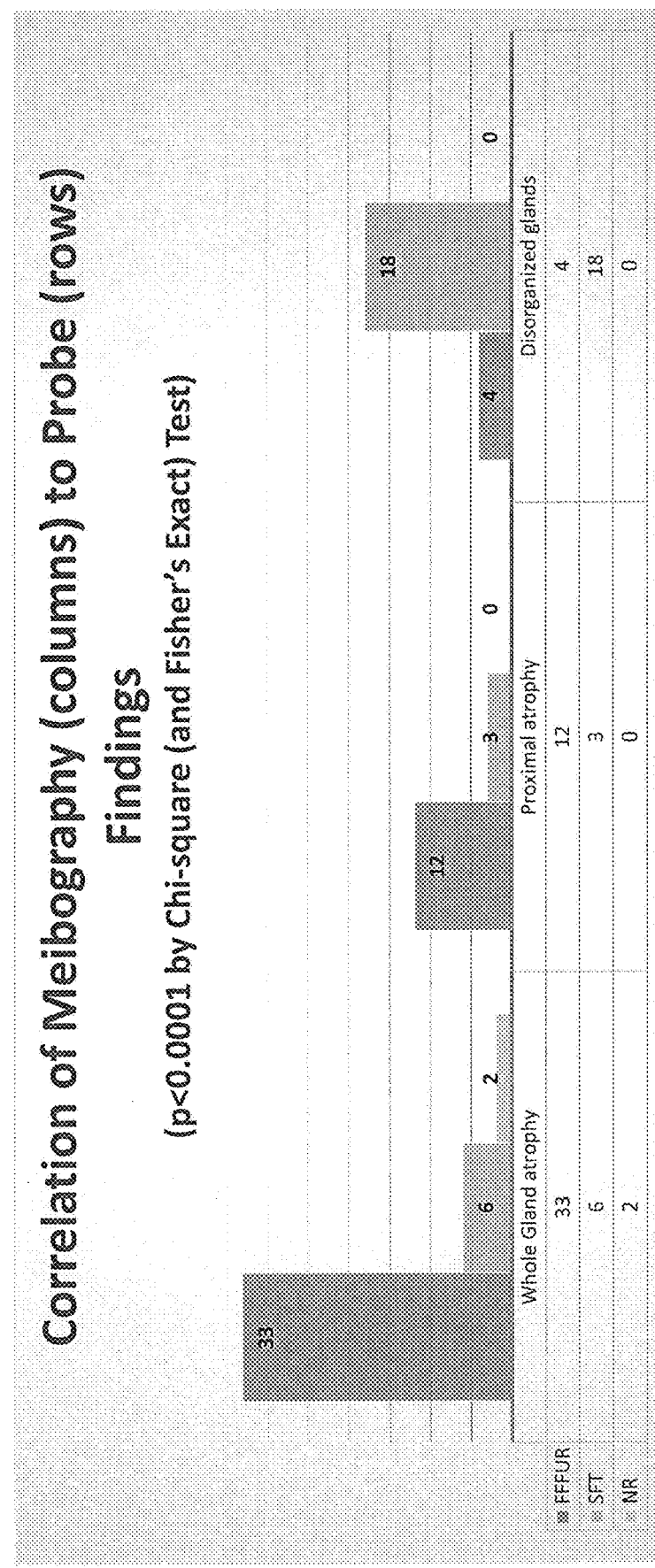
FIG. 3 is a histogram showing correlation of meibography to probe findings.
Figure 4:
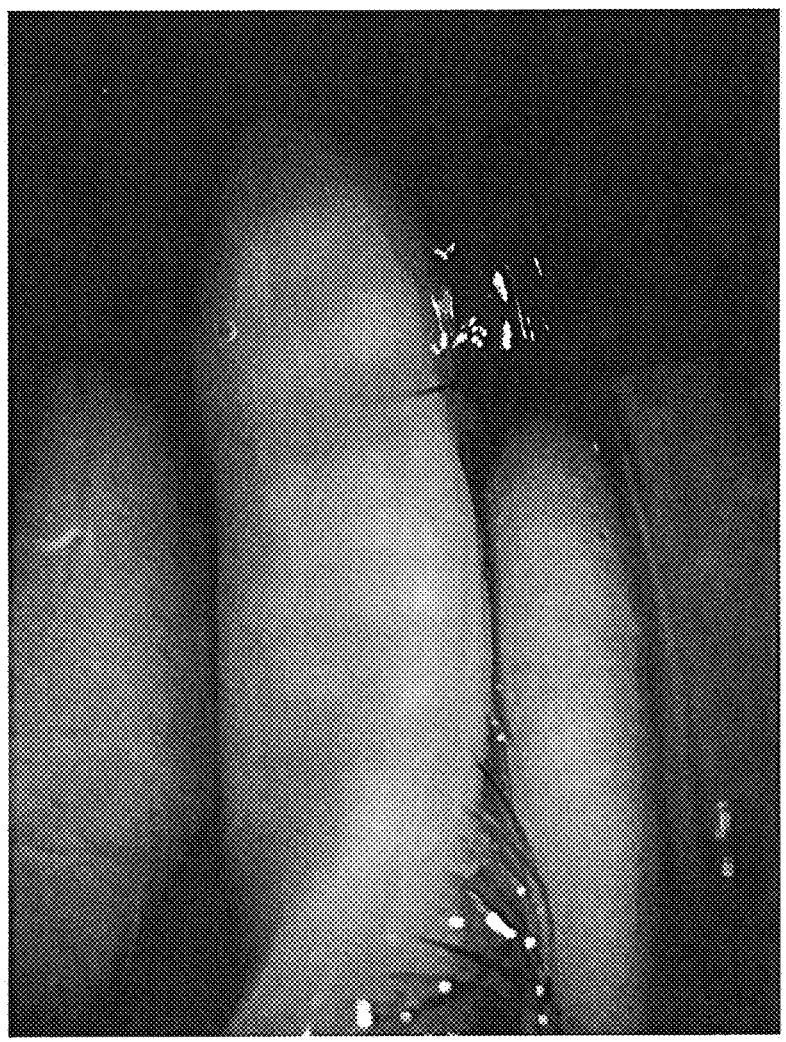
FIG. 4 shows probing where a duct channel exists in the setting of whole gland atrophy and proximal atrophy.

Of 39 glands with whole gland atrophy, 15 glands with proximal atrophy and 22 disorganized glands on meibography, there was a significant difference in FFFUR for whole gland (84.6%) and proximal atrophy (80%) compared with SFT (81.8%) for disorganized glands (p<0.000 by Chi-square and Fisher's Exact test). (Table 1 and FIG. 3 histogram.) (FIG. 3) It was frequently noted that a duct channel exists in the setting of whole gland atrophy and proximal atrophy suggesting that the duct channel may persist despite widespread and complete or partial acinar-ductule loss. (FIG. 4)

Figure 5:
FIG. 5 shows placement of an intraductal polyimide tube which enables retrieval of a meibum specimen.
Figure 6:
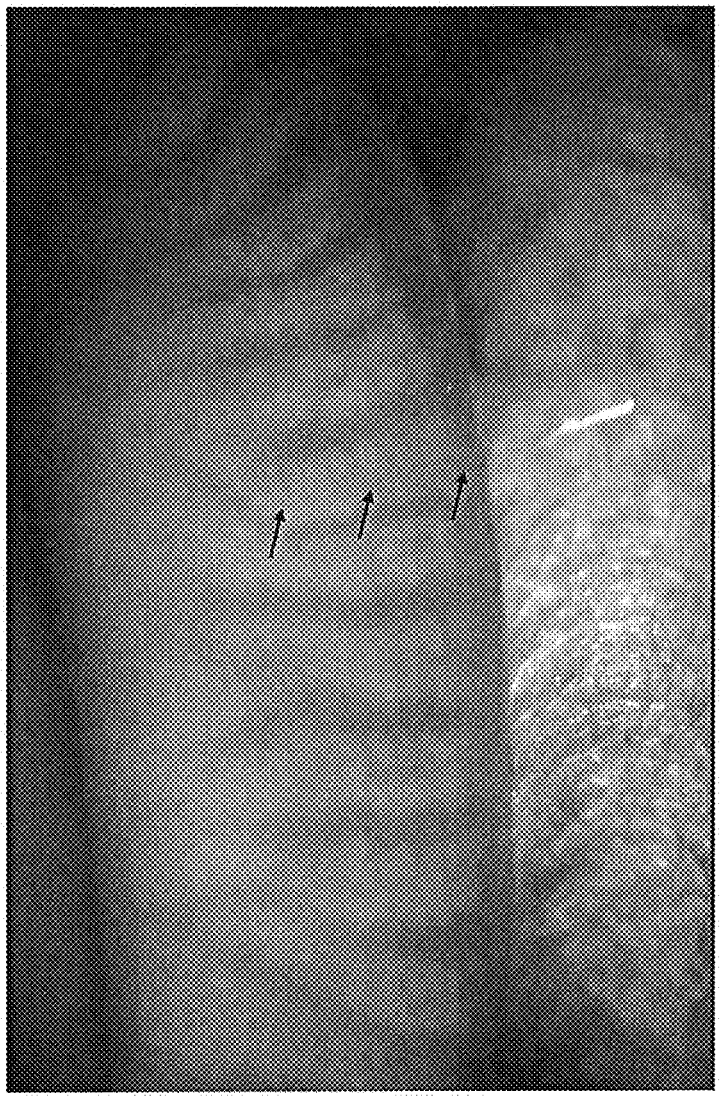
FIG. 6 shows an intraductal polyimide tube which functions as a stent to keep a duct open.

Injection of intraductal dexamethasone using stainless steel microtube showed no distention of gland structures. Placement of intraductal polyimide tube enabled retrieval of meibum specimen. (FIG. 5) and may function as a stent to keep duct open (FIG. 6).

In general, the foregoing embodiments are described for illustrative and exemplary purposes; the present invention is not necessarily limited thereto. Rather, those skilled in the art will appreciate that various modifications, as well as adaptations to particular circumstances, will fall within the scope of the invention as herein shown and described and of the claims appended hereto.

What is claimed is:

1. A method of replacing an atrophic meibomian gland of an eyelid of a patient, the method comprising:
   locating the atrophic meibomian gland having an obstructed orifice in a margin of the eyelid of the patient;
   using a probe to pierce the margin of the eyelid to create a new orifice for a replacement meibomian gland in an area of the margin of the eyelid adjacent to the atrophic meibomian gland having the obstructed orifice, and using the probe to create a central duct channel between the new orifice and an interior space of the replacement meibomian gland;
   placing a microtube in the central duct channel; and
   retaining the new orifice and the central duct channel with the microtube until a lining of the central duct channel is populated with cells to form the replacement meibomian gland and the central duct channel is viable.

* * * * *